United States Patent
Schmit et al.

(10) Patent No.: US 9,522,048 B1
(45) Date of Patent: Dec. 20, 2016

(54) PHYSICAL CABLE LEAD IDENTIFIER FOR MEDICAL SYSTEMS

(71) Applicant: General Electric Company, Schenectady, NY (US)

(72) Inventors: Rodger F. Schmit, Wauwatosa, WI (US); Adrian F. Warner, Wauwatosa, WI (US); Daniel R. Schneidewend, Wauwatsoa, WI (US); Timothy P. Stiemke, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 14/804,825

(22) Filed: Jul. 21, 2015

(51) Int. Cl.
 *A61N 1/375* (2006.01)
 *A61B 5/042* (2006.01)
 *G08B 5/36* (2006.01)
 *A61B 5/00* (2006.01)

(52) U.S. Cl.
 CPC .............. *A61B 90/92* (2016.02); *A61B 5/042* (2013.01); *A61B 5/742* (2013.01); *G08B 5/36* (2013.01)

(58) Field of Classification Search
 None
 See application file for complete search history.

(56) References Cited

U.S. PATENT DOCUMENTS

| | | | |
|---|---|---|---|
| 7,404,716 B2 | 7/2008 | Gregorio et al. | |
| 7,715,908 B2 * | 5/2010 | Moran | A61B 5/042 600/522 |
| 7,963,773 B2 | 6/2011 | Palli et al. | |
| 8,206,175 B2 * | 6/2012 | Boyd | A61N 1/375 439/490 |
| 2003/0028886 A1 | 2/2003 | Wang et al. | |
| 2013/0030482 A1 | 1/2013 | Warner et al. | |
| 2014/0210631 A1 | 7/2014 | Zavis | |

* cited by examiner

*Primary Examiner* — Brian T Gedeon
(74) *Attorney, Agent, or Firm* — Boyle Friedrickson, S.C.

(57) ABSTRACT

In the present invention, an electrophysiology (EP) mapping or recording device for obtaining and recording information on a patient connected to the EP system includes a central processing unit (CPU), a display connected to the CPU, a catheter connected to the CPU by a catheter input module and configured to supply a physiological signal to the CPU via the input module and a catheter identification system connected between the input module catheter and the CPU. The identification system includes a driver circuit that communicates with the CPU to determine a color of a visual representation of the signal from the catheter on the display and a light source connected to the driver circuit. The light source is operated by the driver circuit to emit light corresponding to the color of the representation on the display to identify the catheter in conjunction with the representation on the display.

20 Claims, 4 Drawing Sheets

PHYSICAL CABLE LEAD IDENTIFIER FOR MEDICAL SYSTEMS

BACKGROUND OF INVENTION

The invention relates generally to identification systems for cable leads or catheters, and more particularly to identification systems that enable the cable leads or catheters to be specifically identified by and correlated to the visual representation of the signal from the catheter on the display of the electrophysiological (EP) or other recording or mapping device or system to which the catheters are connected during studies or monitoring of patients.

Catheters are used in an increasing number of medical procedures to evaluate various conditions of the patient with which the catheter is utilized. While many different numbers and/or configurations of catheters can be utilized for a particular procedure, for each procedure all of the catheters in use must be properly connected to the recording or mapping device such that the signals received from or sent to a particular catheter are correctly identified and displayed by the recording or mapping device.

To identify the particular catheter to the associated recording or mapping device, the catheters are connected to an input module, such as a pin box or other suitable connector, used with the recording or mapping device. Each catheter is connected to a specific location or port on the pin box that corresponds to a particular location in the patient at which the catheter is positioned during the performance of the procedure. This location or port is additionally associated with a particular signal display on the a screen of the recording or mapping device, such that during the procedure signals received from or sent to the catheter at that port are illustrated on the display in the field corresponding to that port.

During initial set up and connection of the catheters to perform a procedure, on many occasions one or more catheters can be inadvertently connected to the incorrect ports, such that incorrect signals are represented on the display viewed by the clinician. This results at least in requiring the clinician or other individual to check the catheter connections for the incorrect connection, but can also result in a misdiagnosis of a patient on which the procedure is being performed. Further, in a situation where the catheter is defective and providing a faulty or no signal, if the catheter is incorrectly placed in the pin box, the determination of the faulty electrode, bad lead, and/or unintended disconnect is relatively straightforward with basic physiological instrumentation using a single catheter. However, this challenge increases exponentially with complex patient studies such as performed in cardiac electrophysiology where catheter/lead sets of up to 250+ individual catheters are possible, such as when using complex mapping catheters, for example, that can include up to seven (7) separate input modules, connectors or pin boxes, each with up to thirty-two (32) separate ports thereon. In these situations, the incorrect placement of a catheter that is functioning incorrectly can result in a misdiagnosis of the patient.

Accordingly, it is desirable to develop an identification system and method for the proper association of a catheter to a display of signals sent to or received from the catheter on a mapping or recording system to which the catheter is connected for use in a medical procedure. The identification system should allow an easy and readily observable identification of the catheter at the input connection corresponding to the signal display on the system.

BRIEF DESCRIPTION OF THE INVENTION

There is a need or desire for a system to visually identify or associate a catheter connected to an input for a mapping or recording system to a specific signal displayed on a recording or mapping system to which the catheter has been connected. The above-mentioned drawbacks and needs are addressed by the embodiments described herein in the following description.

According to one exemplary aspect of the invention, a catheter identification system includes an input module, such as a pin box or other suitable connector for the catheter that includes a number of ports capable of receiving a catheter therein. The input module/pin box is in turn connected to an electrophysiological (EP) or other recording or mapping device or system, such that signals received from or sent to the catheters can be monitored by the device. In order to correlate the catheters engaged with the various ports on the pin box with the displays presented by the device or system, the pin box includes a light source, such as a light emitting diode (LED), disposed on the pin box adjacent each port. When a catheter is connected to a port on the pin box, a central processing unit (CPU) for the display on the device can send a signal to a controller located within the input module/pin box for the light source to operate the light source to correspond to the color of the signal from the catheter connected at that port on the display. Thus, when a signal on the display appears erratic or incorrect for any of a number of reasons, the clinician can simply look at the pin box to locate the port at which the color of the light source corresponds to the color of the signal on the display. In this manner, the pin box can efficiently direct the clinician to the catheter at issue, eliminating the need to review the connections for multiple catheters to locate any problems.

According to another aspect of an exemplary embodiment of the invention, the controller for the light source can receive signals from the CPU for the device in addition to the signals corresponding the coloration of the light source. For example, if the device is sending an ablation signal to a particular catheter, the controller can operate to control the light source to reflect the signal being sent to the particular catheter, such as by modulating the light source in accordance with the signal being sent, e.g., flashing the light source. In this manner the clinician can readily identify the connection of the catheter to the input module/pin box if issues arise with respect to the signals being sent and the results obtained from the signals. This modulation of the light source can also take place when the signals received from the catheter at issue include a high level of noise or excessive impedance. When the noise or impedance is detected by the CPU, the controller, under the direction of the CPU, can operate the light source to identify the catheter from which the signal including the excessive noise or impedance is coming.

According to still another aspect of an exemplary embodiment off the invention, the CPU can be operated to send a trace signal to the controller of the input module/pin box in order to cause the controller to modulate the light source associated with a port for a catheter from which a signal of interest is coming. The trace function/signal can then cause the controller to operate the light source in a manner to enable the clinician to quickly identify the catheter providing the signal.

According to still a further aspect of an exemplary embodiment of the invention, the light sources can be disposed on the end of the catheter that is engaged with the input module/pin box. In this exemplary embodiment, the controller in the input module/pin box can activate and modulate the operation of the light source in the catheter in accordance with the operation of the display and the device.

According to still another aspect of one exemplary embodiment of the invention, a catheter identification system for associating a catheter connected to an electrophysiology (EP) recording or mapping device with a visual representation of a signal from the catheter on a display for the device includes a driver circuit operably connectable to the device and configured to communicate with a central processing unit of the device to determine a color of the visual representation of the signal on the display and a light source operably connected to the driver circuit, wherein the light source is operated by the driver circuit to emit light corresponding to the color of the visual representation on the display.

According to still a further aspect of one exemplary embodiment of the invention, an EP device for obtaining and recording information on a patient connected to the EP system includes an amplifier including a catheter input module, a computer operably connected to the amplifier and including a central processing unit connected to the amplifier and a display connected to the central processing unit, at least one catheter connected to the catheter input module and configured to supply a physiological signal to the computer via the input module and amplifier and a catheter identification system operably connected between the input module catheter and the central processing unit, the identification system including a driver circuit configured to communicate with the central processing unit to determine a color of a visual representation of the signal on the display and a light source operably connected to the driver circuit, wherein the light source is operated by the driver circuit to emit light corresponding to the color of the visual representation on the display.

According to still a further aspect of one exemplary embodiment of the invention, a method of identifying a catheter connected to an EP device having a display includes the steps of providing a catheter identification system operably connected between a catheter input module an a central processing unit of the EP device, the identification system including a driver circuit configured to communicate with the central processing unit to determine a color of a visual representation of a signal from the catheter on the display and a light source operably connected to the driver circuit, wherein the light source is operated by the driver circuit to emit light corresponding to the color of the visual representation on the display, connecting the catheter to the catheter input module, determining the color of the representation of the signal for the catheter on the display and operating the light source to emit a color corresponding to the color of the representation of the signal on the display.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The drawings illustrate the best mode presently contemplated of carrying out the disclosure. In the drawings

DETAILED DESCRIPTION OF THE DRAWINGS

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
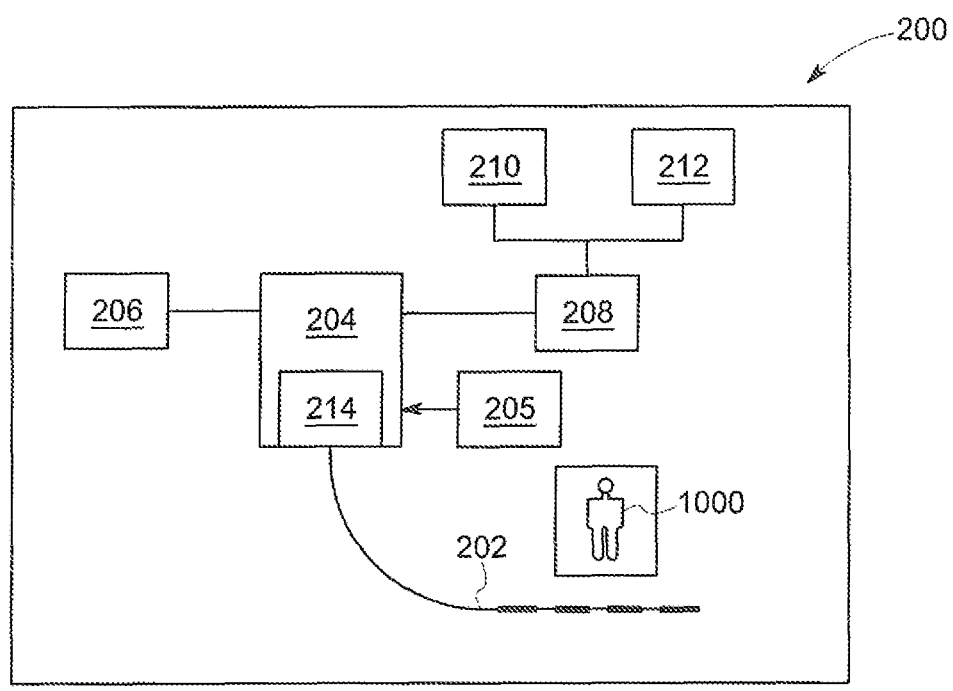
FIG. 1 is a schematic representation of an EP recording system including a catheter identification system according to one exemplary embodiment of the present invention.

FIG. 1 illustrates one exemplary embodiment of an electrophysiology (EP) mapping or an EP recorder system 200, such as those used in intracardiac electrocardiography (ECG) studies within the body of a patient 1000. These systems 200 apply/receive an electrical signal (e.g., electrical current) via one or more catheters 202 to various locations of the body of the patient 1000, such as the heart. The system 200 can be similar to that disclosed in US Patent Application Publication No. US2013/0030482, which is expressly incorporated herein in its entirety. In the exemplary illustrated embodiment, the system 200 includes an amplifier 204 that is operably connected between a signal generator 206 and a suitable computer, controller or central processing unit (CPU) 208. In operation, signals generated by the signal generator 206 are transmitted to the catheter 202 by the amplifier 204. A return signal from the patient 1000, such as an ECG signal, is received by the amplifier 204 either via the catheter 202 or another catheter or device 205, and is processed by the amplifier 204 prior to transmitting the return signal to the CPU 208. The CPU 208 performs additional functions on the return signal and displays the information provided by the return signal on one or both of a real-time display 210 and a review display 212. The displays 210,212 illustrate the information obtained from the each of the various return signals in graphs, numbers or other manners with different colors to enable the clinician viewing the displays to readily distinguish the information provided by the various signals from one another.

Figure 2:
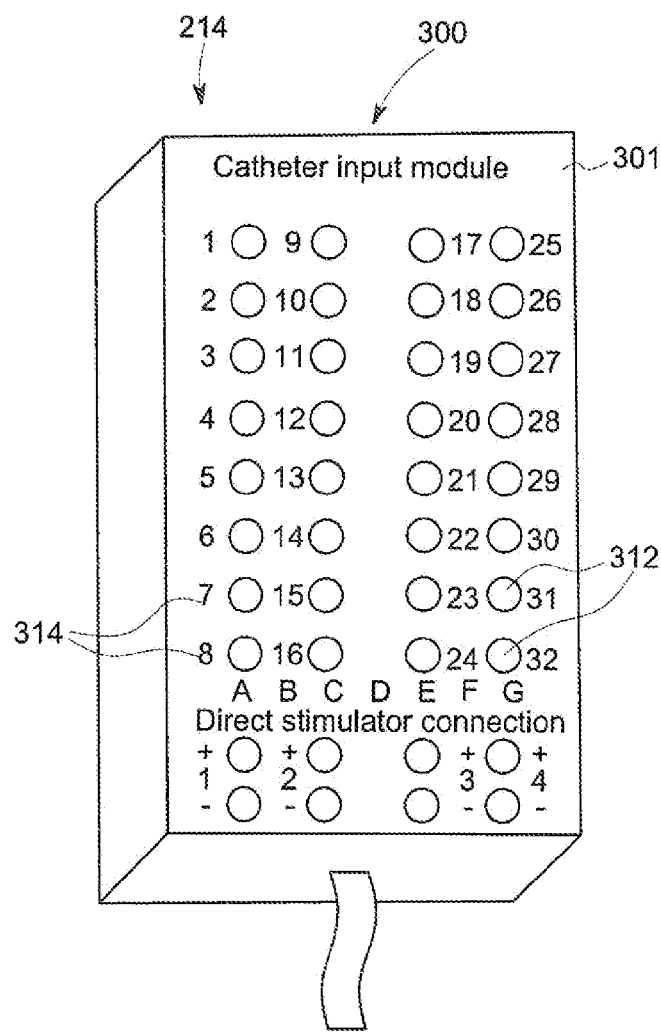
FIG. 2 is a schematic representation of the catheter input module for the recording system of FIG. 1 according to an exemplary embodiment of the invention.

In FIGS. 1 and 2, the amplifier 204 also includes a catheter input module 214 that is used to connect the catheter 202 to the amplifier 204 for use with the recording or mapping system 200. In one exemplary embodiment of the catheter input module 214, such as a pin box, is illustrated. The input module 214 includes a number of ports 216 that are configured to receive corresponding pins (not shown)

disposed on the catheter 202 in order for the catheter 202 to be electrically coupled to the input module 214, and thus enable electric signals to pass between the input module 214 and the catheter 202. The ports 216 are each connected to a catheter signal analog-to-digital converter (ADC) circuit (not shown) within the amplifier 204 in order to convert the analog signals from the catheter 202 into digital signals that can be output from the ADC circuit to the CPU 208 via the amplifier 204.

Figure 3:
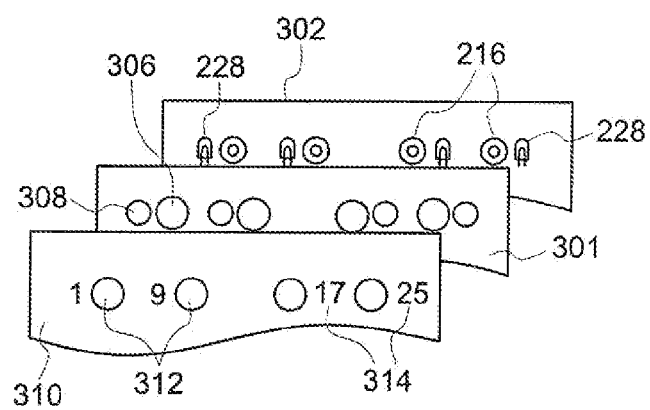
FIG. 3 is a partially broken away, exploded view of the input module of FIG. 2 according to an exemplary embodiment of the invention.
Figure 4:
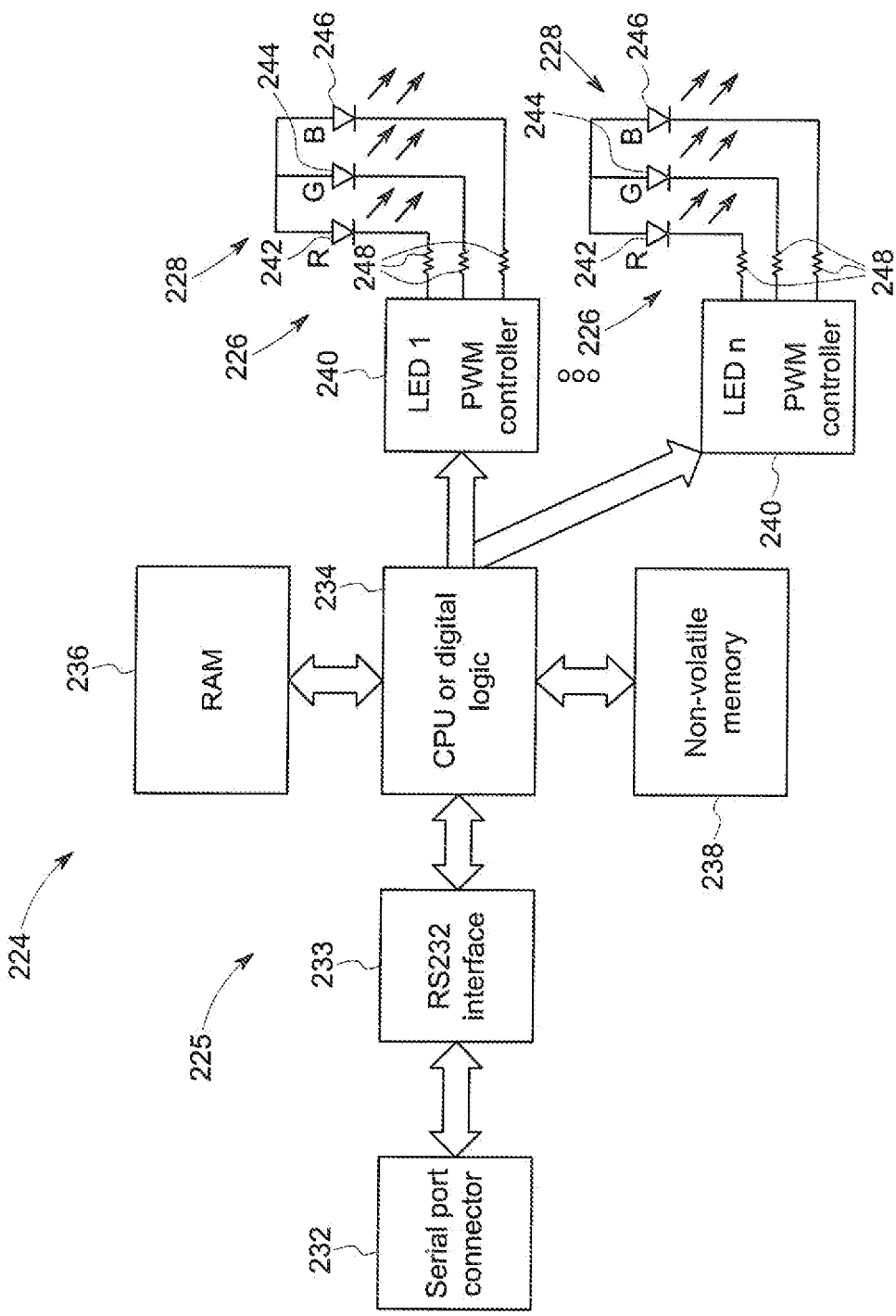
FIG. 4 is schematic view of the input module according to another exemplary embodiment of the invention.

The input module 214 additionally includes a catheter identifier system 224, with one exemplary embodiment of the system 224 illustrated in FIGS. 2-4. The identifier system 224 is formed within the input module 214 and includes a driver circuit 225 having a number of light sources 226 disposed adjacent each of the ports 216. In one embodiment, the light sources 226 are multicolor light emitting diodes (LEDs) 228 that are programmed/operated by the driver circuit 225 and driver circuit controller 234 to mimic the color of the display of the signal from the particular catheter 202 connected to the associated port as that signal is illustrated on the display 210,212. In this manner, the system 224 allows a user to rapidly locate the catheter 202 associated with a video display signal relative to the color of the display signal thus allowing rapid identification of the catheter 202 sourcing the particular signal to the device 200. The light sources 226 corresponding to non-displayed signals from the associated catheters 202 connected to the input module 214 remain extinguished further assisting the clinician in rapidly identifying the catheters 202 acting as sources of the signals being displayed.

The input module 214 in one exemplary embodiment in FIGS. 2 and 3 includes a housing 300 having a front face 301. The driver circuit 225 is disposed within the housing 300, with each port 216 is connected at an inner end (not shown) to the driver circuit 225. Disposed on the circuit board 302 adjacent the inner end of the ports and/or direct stimulator connections 216 is a multicolor LED 228. The front face 301 of the housing 300 includes a number of first openings 306 disposed over and aligned with each of the ports 216 in order to enables access by the catheters 202 to the ports 216. The front face 301 also includes a number of second openings 308 located adjacent the first openings 306 and disposed over and aligned with the LEDs 228. The second openings 308 allow light emitted from the LEDs 228 to pass through the second openings 308. The input module 214 also includes an overlay or cover 310 disposed over the front face 301 of the housing 300. The overlay 310 includes apertures 312 that are aligned with the first openings 306 to enable access to the ports 216. The overlay 310 also includes printed identifiers 314 disposed over the second openings 308 adjacent the apertures 312. When the LEDs 228 are activated, the light emitted from the LEDs 228 can be viewed through the second openings 308 and illuminate the identifiers 314.

Figure 5:
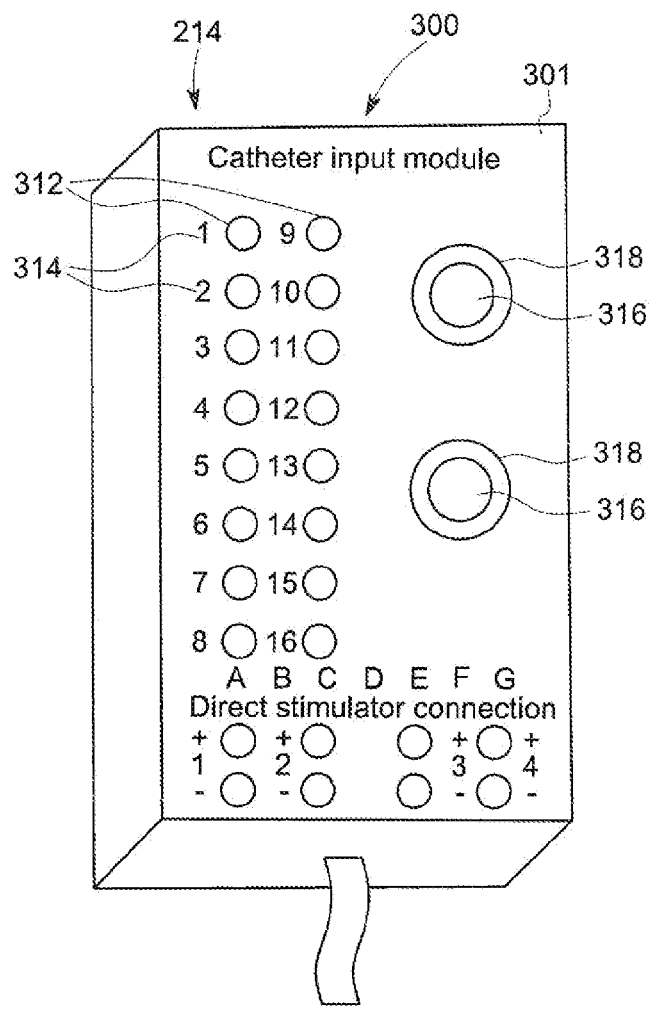
FIG. 5 is a schematic representation of the catheter input module for the recording system of FIG. 1 according to another exemplary embodiment of the invention.
Figure 6:
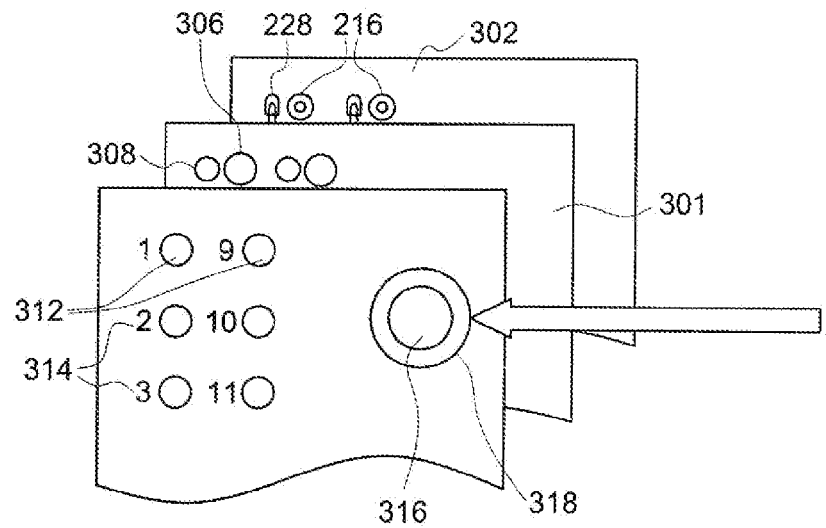
FIG. 6 is a partially broken away, exploded view of the input module of FIG. 5 according to an exemplary embodiment of the invention.

An alternative exemplary embodiment of the input module 214 is illustrated in FIGS. 5 and 6. In this embodiment, the general construction of the input module 214 including the housing 300 and overlay 310 remains the same. However, the housing 300 includes a fewer number of ports 216 and instead includes a catheter connection 316 having a configuration for the connection with a different style of catheter 202. The connection 316 also has one end in connection with the driver circuit 225 and as an alternative to the LED 228, is formed with a light source 226 formed as a light pipe 318 positioned around the circumference of the connection 316 that directs light emitted from the LEDs 228 around the connection 316 to identify the connection 316 with the associated information on the display 210,212, in a manner to be described.

Referring now to FIG. 4, one embodiment of the system 224 and the driver circuit 225 is illustrated. The driver circuit 225 includes a serial connector 232, or equivalent, that is used to connect to and facilitate communication from the CPU 208 to an isolated independently powered driver circuit controller 234 located within the input module 214 via an interface 233. The controller 234 is operably connected to an over-writable or random access memory module (RAM) 236 and to a non-volatile or read-only memory module (ROM) 238. Each memory module 236,238 includes storage for various information to be utilized by the controller 234 in operating the LEDs 228 that are also operably connected to the controller 234. The RAM module 236 can store information relating to the particular configuration of the catheters 202 connected to the input module 214 for the particular procedure and the colors to be applied for the information display from each of the catheter 202, which can be altered, such as by the clinician, to accommodate different catheter configurations for different procedures. The ROM module 238 contains information regarding different operational parameters of the input module 214 that remain constant between different procedures.

When the catheter 202 is connected to the input module 214, the controller 234 operably connects the display LED 228 with the serial connector 232 and the catheter 202. In this manner there is created an association via the CPU 108 and driver circuit controller 234 between the indicator LED 228 for the particular catheter 202 and the illustration of the information from the catheter 202 on the displays 210,212 of the device 200. In this creating this association, the LED 228 is operated by the driver circuit controller 234 using a decode processing logic such that the multi-color indicator LED 228 can have a 32-bit color palette, or a palette as is defined by the current state of art. As shown in the exemplary embodiment of FIG. 4, to function in this manner the LEDs 228 are multi-chromatic light sources that each include a pulse width modulation (PWM) controller 240 that is connected via resistors 248 to a number of diodes 242, 244 and 246 which emit red, green and blue light, respectively. Each diode 242, 244, 246 can be operated by the PWM controller 240 under the direction of the controller 234 to emit light of a specified intensity. The intensity of the light emitted from each diode 242, 244, 246 is controlled such that the combined spectrums of the light emitted corresponds to the color of the information from the catheter 202 associated with the particular LED 228 on the display 210,212. In this manner, the LEDs 228 are operated by the controller 234 to provide a readily ascertainable visual indication of the location of the catheter 202 corresponding to the information on the displays 210,212 via the association of the color of the information on the display 210,212 and the color emitted by the individual LEDs 228.

In addition to the ability to identify the location of the catheter 202 on the input module 214 that is the source of the signal/information of interest using color alone, the system 224, driver circuit 225 and controller 234 can also have alternate display properties for the LEDs 228. These display properties can include the ability for the driver circuit 225 and/or controller 234 to operate the LEDs 228 to flash once, flash repetitively, and an infinite variety of pulse on/off patterns as defined by the driver circuit 225 and stored in memory module 238.

In operation, when the input module 214 is connected to the recorder or mapping device 200, the identification system 224 and driver circuit 225 is operably connected to the CPU 208 of the system 200. This enables the configuration for the catheters 202 for the particular procedure to be performed to be relayed to the system 224 such that the various ports 216 can be linked with the signals to be illustrated on the displays 210,212. In this manner, the LEDs 228 at the signal source, i.e., the catheter 202, are "slaved" to the device display 210,212 such that the color used for representing the signal on the display 210,212 and its properties may be replicated at the respective LED 228 at the signal source by the driver circuit 225 relative to the user interface properties and user instruction provided to the device 200 and system 224. In one example, if twenty (20) channels of intercardiac signals, each signal obtained from a separate catheter 202, are being represented on a display 210,212 of a physiological recording device 200, then twenty (20) LEDs 228 will be illuminated on the catheter input module 214 at the ports 216 for each of the catheters 202 connected to the input module 214, with each diode 242,244,246 of the LED 228 illuminated to provide a unique color combination for the LED 228 that matches the color of the representation of the information provided by the catheter 202 associated with the particular LED 228 on the display.

Further, other diagnostic features of the device 200 can be applied to and through the identification system 224 to assist in determining any faults in the operation of the device 200 during the procedure. For example, through an interface (not shown) for the device 200, the clinician can select a trace function for the device 200. This trace function enables the clinician to select a portion of the display 210,212 representing a particular signal and have the LED 228 associated with that signal operated in a pre-determined manner by the identification system 224 to identify the signal source, i.e., the catheter 202, thus "tracing" the displayed information from the display 210,212 to its source. This same function can alternatively or concurrently be utilized when signals or pulses (such as those utilized in an ablation procedure) are directed by the clinician from the device 200 to a particular catheter 202 in the procedure, thereby enabling the clinician to visually identify the catheter 202 that actually is receiving the signals from the device 200 as indicated on the display 210,212.

Further, in a situation where a signal or channel received by the device 200 and represented on the display 210,212 has one or more anomalies associated with the signal, such as, for example, if the signal is subject to excessive noise, the CPU 208 would detect the noise level in the signal and alter the representation of the signal/channel on the display 210,212 this in a pre-determined manner, such as by providing a series of pulsed label warnings for the channel on the display 210,212. The warning provided by the CPU 208 on the display 210,212 can be transmitted to the identification system 224 and replicated by the driver circuit 225 in an appropriate manner at the corresponding LED 228 to identify the catheter 202 subject to the excessive noise. Alternatively, the identification of the catheter 202 at issue can be provided by a light source 226 that is associated with a particular catheter or cable 202 in the manner described previously, but is located other than on the input module 214, such as on located on the cable lead (not shown) at the patient 1000, or at the catheter connector (not shown) or at some other location in close proximity to the catheter 202, or at any number of these locations in combination with one another. In this manner, the system 224 can provide a visual indication for a number of situations regarding the signals sent to and received from a catheter 202 connected to the device 200 via the system 224, such as automated catheter failure, manual lead detection, and simple lead association.

Other exemplary embodiments for the identification system 224 can include coloring the end of the catheter 202 engaged with the input module 214 and then using the interface of the device 200 to manually associate the catheter color with the corresponding color utilized on the input module 214 and/or the display 210,212. Additionally, instead of manually entering the information regarding the catheter color, the system 224 can detect the color in some suitable manner, such as by using a sensing resistor (not shown) within the catheter 202 that is analyzed by the system 224 upon connection of the catheter 202 to the input module 214 to identify the color from the resistor(s) and then to program the display 210,212 with the appropriate color for that catheter signal. Still another exemplary embodiment could include a color select control (not shown) at the input module 214 from which the clinician can select the display color for the particular catheter 202 at that connection, thus identifying the color to be utilized for the signals coming from that connection on the display 210,212. This color selection "dial" can also be provided at the interface of the device 200 such that the selection of the color for the display 210,212 would be reference by the LEDs 228 at the port 216 of the input module 214 for that particular catheter 202.

With a device 200 employing a catheter/lead/cable identification system 224 of this type, the system 224, among other benefits, provides a visual and easily observable association between the signals represented on the display and the catheter from which the signal(s) originated, provides set up and checking of the catheter/device connections and provides faster resolution/debugging of complex wiring scenarios, such as those associated with cardiac EP procedures and studies.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A catheter identification system for associating a catheter connected to an electrophysiology (EP) recording or mapping device with a visual representation of a signal from the catheter on a display for the device, the identification system comprising:
   a) a driver circuit operably connectable to the device and configured to communicate with a central processing unit of the device to determine a color of the visual representation of the signal on the display; and
   b) a light source operably connected to the driver circuit, wherein the light source is operated by the driver circuit to emit light corresponding to the color of the visual representation on the display.

2. The identification system of claim 1 wherein the light source is a multi-chromatic light source.

3. The identification system of claim 2 wherein the light source is a multi-chromatic LED.

4. The identification system of claim 1 further comprising an input module within which the driver circuit and light source are positioned.

5. The identification system of claim 4 wherein the input module comprises:
   a. a number of connection ports each adapted to engage a catheter inserted therein; and
   b. a number of light sources, each light source disposed adjacent a connection port and operably connected to the driver circuit.

6. The identification system of claim 5 wherein the number of light sources are each enclosed within the input module.

7. The identification system of claim 1 wherein the driver circuit comprises:
   a. a connector operably engageable with the mapping and recording device;
   b. a circuit controller operably connected to the light source and to the connector, the circuit controller configured to communicate with the mapping and recording device via the connector to selectively operate the light source.

8. The identification system of claim 7 further comprising an over-writable memory module operably connected to the circuit controller, the over-writable memory module configured to receive and retain information concerning a particular configuration for the device for use by the circuit controller in operating the light source.

9. The identification system of claim 7 further comprising a non-volatile memory module operably connected to the circuit controller, the non-volatile memory module configured to retain information concerning operational parameters of the device for use by the circuit controller in operating the light source.

10. The identification system of claim 9 wherein the light source is a multi-chromatic LED.

11. The identification system of claim 10 wherein the circuit controller is configured to operate the multi-chromatic LED to emit light of different intensities from various diodes forming the LED.

12. An EP device for obtaining and recording information on a patient connected to the EP system, the EP device comprising:
   a. an amplifier including a catheter input module;
   b. a computer operably connected to the amplifier and including a central processing unit connected to the amplifier and a display connected to the central processing unit;
   c. at least one catheter connected to the catheter input module and configured to supply a physiological signal to the computer via the input module and amplifier; and
   d. a catheter identification system operably connected between the input module catheter and the central processing unit, the identification system comprising:
      i. a driver circuit configured to communicate with the central processing unit to determine a color of a visual representation of the signal on the display; and
      ii. a light source operably connected to the driver circuit, wherein the light source is operated by the driver circuit to emit light corresponding to the color of the visual representation on the display.

13. The EP device of claim 12 wherein the driver circuit comprises:
   a. a connector operably engageable with the central processing unit;
   b. a circuit controller operably connected to the light source and to the connector, the circuit controller configured to communicate with the central processing unit via the connector to selectively operate the light source.

14. The EP device of claim 12 wherein the input module comprises:
   a. a number of connection ports engageable with the at least one catheter; and
   b. a number of light sources, each light source disposed adjacent a connection port and operably connected to the driver circuit.

15. The EP device of claim 14 wherein each light source is a multi-chromatic LED.

16. The EP device of claim 15 wherein the circuit controller is configured to operate each multi-chromatic LED to emit light of different intensities from various diodes forming the LED.

17. A method of identifying a catheter connected to an EP device having a display, the method comprising the steps of:
   a) providing a catheter identification system operably connected between a catheter input module an a central processing unit of the EP device, the identification system including a driver circuit configured to communicate with the central processing unit to determine a color of a visual representation of a signal from the catheter on the display and a light source operably connected to the driver circuit, wherein the light source is operated by the driver circuit to emit light corresponding to the color of the visual representation on the display;
   b) connecting the catheter to the catheter input module;
   c) determining the color of the representation of the signal for the catheter on the display;
   d) operating the light source to emit a color corresponding to the color of the representation of the signal on the display.

18. The method of claim 17 wherein the step of operating the light source further comprises the step of altering the operation of the light source in response to anomalies detected by the central processing unit in the signal from the catheter.

19. The method of claim 17 wherein the step of operating the light source further comprises the step of altering the operation of the light source in response to activation of a tracing function in the central processing unit.

20. The method of claim 17 wherein the step of operating the light source further comprises the step of altering the operation of the light source in response to sending pulses to the catheter from the central processing unit.

* * * * *